United States Patent
Isaacs et al.

(10) Patent No.: US 12,357,391 B2
(45) Date of Patent: Jul. 15, 2025

(54) TRACKING ELEMENTS FOR USE IN SYSTEMS AND METHODS FOR IMAGE LOCALIZATION OF EFFECTERS DURING A MEDICAL PROCEDURE

(71) Applicant: TrackX Technology, Inc., Chapel Hill, NC (US)

(72) Inventors: Robert E. Isaacs, Chapel Hill, NC (US); David A. Skwerer, Raleigh, NC (US); Farah Hamouda, Raleigh, NC (US)

(73) Assignee: TrackX Technology, Inc., Hillsborough, NC (US)

(*) Notice: Subject to any disclaimer, the term of this patent is extended or adjusted under 35 U.S.C. 154(b) by 734 days.

(21) Appl. No.: 17/217,679

(22) Filed: Mar. 30, 2021

(65) Prior Publication Data

US 2021/0298837 A1    Sep. 30, 2021

Related U.S. Application Data (60) Provisional application No. 63/001,711, filed on Mar. 30, 2020.

(51) Int. Cl.
*A61B 90/00* (2016.01)
*A61B 34/20* (2016.01)

(52) U.S. Cl.
CPC .............. *A61B 34/20* (2016.02); *A61B 90/39* (2016.02); *A61B 2034/2055* (2016.02); *A61B 2034/2059* (2016.02)

(58) Field of Classification Search
CPC . A61B 34/20; A61B 90/39; A61B 2034/2055; A61B 2034/2059
See application file for complete search history.

(56) References Cited

U.S. PATENT DOCUMENTS

| | | | |
|---|---|---|---|
| 2007/0203562 A1* | 8/2007 | Malewicz | A61M 25/1011 623/1.34 |
| 2014/0249614 A1* | 9/2014 | Levi | A61F 2/07 623/1.2 |
| 2015/0119685 A1* | 4/2015 | Daon | A61B 34/20 600/407 |
| 2018/0043133 A1* | 2/2018 | Wong | A61M 25/0108 |
| 2020/0281660 A1* | 9/2020 | Homan | G06V 40/16 |

* cited by examiner

*Primary Examiner* — Rochelle D Turchen
(74) *Attorney, Agent, or Firm* — Maginot, Moore & Beck, LLP (57) ABSTRACT

A surgical effecter, such as a tool, implant or instrument, or a tracking element mounted to the surgical effecter, includes an elongated shaft with a marker affixed thereon that is detectable by cameras or detectors of a localizer or tracking system configured to track the position and orientation of the effecter during a surgical procedure. The marker is wrapped around the circumference of the shaft and presents a top edge and a bottom edge that are perpendicular to the longitudinal axis of the shaft, and a visible spiral edge extending from the top edge to the bottom edge.

10 Claims, 7 Drawing Sheets

TRACKING ELEMENTS FOR USE IN SYSTEMS AND METHODS FOR IMAGE LOCALIZATION OF EFFECTERS DURING A MEDICAL PROCEDURE

PRIORITY CLAIM

This application is a utility filing from and claims priority to U.S. Provisional Application No. 63/001,711, filed on Mar. 30, 2020, the entire disclosure of which is incorporated herein by reference.

BACKGROUND

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries and interventions that are in effect guided by serial imaging, which we will refer to as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoro unit, also known as a C-arm. The C-arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A DRR is a digital representation of an X-ray made by taking a CT scan of a patient and simulating taking X-rays from different angles and distances. The result is that any possible X-ray that could be acquired for that patient can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken in the operating room (OR).

Many imaging approaches, such as taking fluoro images, involve exposing the patient to radiation, albeit in small doses. However, in these image guided procedures, the number of small doses adds up so that the total radiation exposure can be problematic not only to the patient but also to the surgeon or C-arm technologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Collimators are available that can specially reduce the area of exposure to a selectable region. For instance, a collimator, such as the Model Series CM-1000 of Heustis Medical, is placed in front of an x-ray source, such as the source 104 shown in FIG. 1. The collimator consists of a series of plates that absorb most incident X-rays, such as lead. The only x-rays that reach the patient are those that pass through apertures between the plates. The position of the plates can be controlled manually or automatically, and the plates may be configured to provide differently shaped fields, such as a multi-sided field. Since the collimator specifically excludes certain areas of the patient from exposure to x-rays, no image is available in those areas. The medical personnel thus have an incomplete view of the patient, limited to the specifically selected area. Thus, while the use of a collimator reduces the radiation exposure to the patient, it comes at a cost of reducing the amount of information available to the medical personnel.

Figure 1:
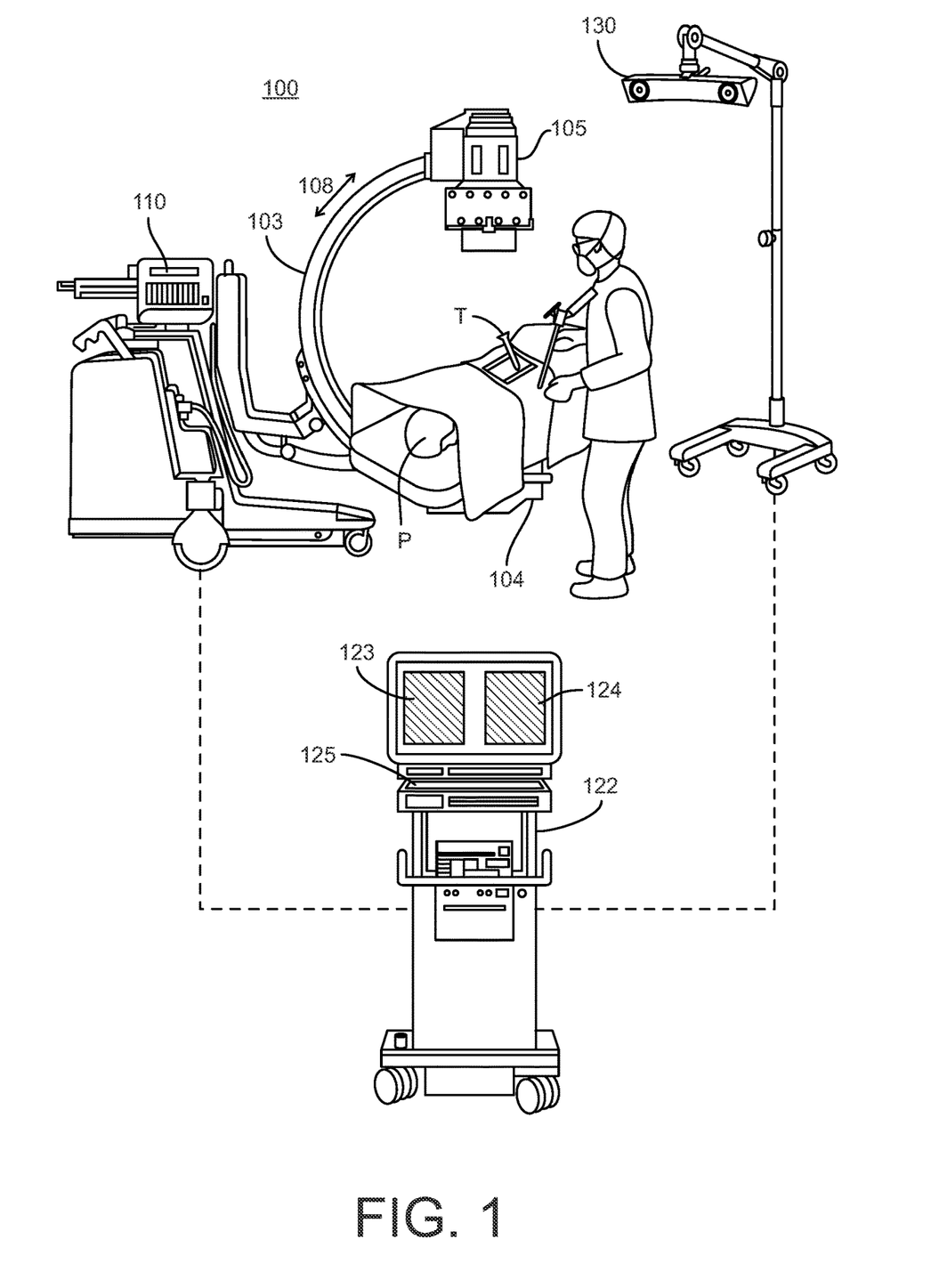
FIG. 1 is a pictorial view of an image guided surgical setting including an imaging system, an image processing device and a localizer or tracking device for surgical instruments and devices.

A typical imaging system 100 is shown in FIG. 1. The imaging system includes a base unit 102 supporting a C-arm imaging device 103. The C-arm includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The source 104 may include a collimator that is configured to restrict the field of exposure. The C-arm 103 may be rotated about the patient P in the direction of the arrow 108 for different viewing angles of the surgical site. In some instances, metal or radio-dense material effecters, such as implants or instruments T, may be situated at the surgical site, necessitating a change in viewing angle for an unobstructed view of the site. Thus, the position of the receiver relative to the patient, and more particularly relative to the surgical site of interest, may change during a procedure as needed by the surgeon or C-arm technologist. Consequently, the receiver 105 may include a tracking target 106 mounted thereto that allows tracking of the position of the C-arm using a tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image or pixel-based image for projection as displays 123, 124 on a display device 126. The displays are positioned for interactive viewing by the surgeon during the procedure. The two displays may be used to show images from two views, such as lateral and AP, or may show a baseline scan and a current scan of the surgical site. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format. In some cases, the C-arm may be operating in the cinematic exposure mode and generating many images each second. In these cases, multiple images can be averaged together over a short time period into a single image to reduce motion artifacts and noise.

Standard X-ray guided surgery typically involves repeated x-rays of the same or similar anatomy as an effecter (e.g.—screw, cannula, guidewire, instrument, etc.) is advanced into the body. This process of moving the effecter and imaging is repeated until the desired location of the instrument is achieved. This iterative process alone can increase the lifetime risk of cancer to the patient over 1% after a single x-ray intensive intervention.

A system and method for image localization of effecters during a medical procedure is disclosed in U.S. Pat. No. 10,825,177 (the '177 Patent), which issued on Nov. 3, 2020, the entire disclosure of which is incorporated herein by reference. A computer-assisted imaging localization system is provided that assists the physician in positioning implants and instruments into a patient's body. The system has the desired effect of displaying the actual instrument or implant and using this displayed to guide surgery without the need to directly interact with the computer. The system does so by displaying and moving overlapping images on a computer screen, allowing one image to be seen through the other. These image "masks" can be the unaltered image or doctored images to intensify or mitigate the anatomical or non-anatomical aspects of the image. Sliding these images over one another can help to position medical devices with a high degree of accuracy with a limited number of additional x-rays.

In another feature of the system and method disclosed in the '177 Patent, tracking elements are provided for a surgical tool or instrument (i.e., effecter) having an elongated shaft and a working tip, that allows the instrument or tool to be tracked by an optical tracking associated with the imaging localization system. In one embodiment, the tracking element includes at least one band at least partially encircling the outside surface of the cylindrical body, in which the band is adapted to be detected by an optical localizer or an optical detection device associated with an x-ray imaging system. The tracking elements allow tracking of the instrument or tool in all degrees of freedom of movement to allow accurately locating the instrument and its working tip relative to the anatomy in the surgical field.

SUMMARY OF THE DISCLOSURE

A surgical effecter, such as a tool, implant or instrument, or a tracking element mounted to the surgical effecter, includes an elongated shaft with a marker affixed thereon that is detectable by cameras or detectors of a localizer or tracking system configured to track the position and orientation of the effecter during a surgical procedure. The marker is wrapped around the circumference of the shaft and presents a top edge and a bottom edge that are perpendicular to the longitudinal axis of the shaft, and a visible spiral edge extending from the top edge to the bottom edge. In particular, the visible edge is oriented non-perpendicular and non-colinear to the longitudinal axis L of the elongated shaft. The spiral edge allows the software of the localizer or tracking system to discern the edge so that the system can accurately determine the centroid of the marker for use in determining the position and orientation of the effecter.

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
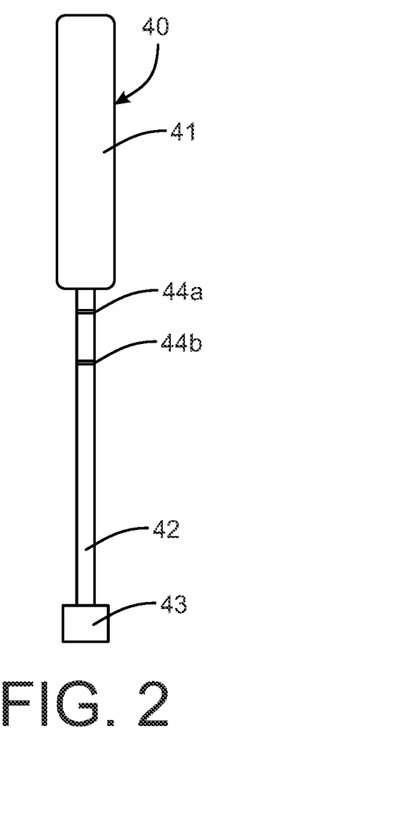
FIG. 2 is a side view of a generic effecter having marker bands used for tracking the position of the effecter.

As described in more detail in the '177 Patent, the working tip of the effecter can be represented on the displayed x-ray image as a slug, or other indicia, in which the position of the slug corresponds to the position of the tip of the effecter relative to the anatomy. The slug helps guide the surgeon and the X-ray technician in the surgical procedure. A localizer system acquires the position of the effecter in certain degrees of freedom of movement (such as X, Y, Z, Pitch, Yaw and Roll) of the fluoroscope as it is acquiring images of the surgical site. Typical localizer systems utilize an array of optical sensors to track an optical tracking component mounted to the end of the effecter. An effecter, such as effecter 40 in FIG. 2, includes a handle 41 with an elongated shaft 42 terminating in a working tip 43. The shaft 42 is provided with optically trackable markers 44a, 44b in the form of optical bands that encircle the shaft so that the markers are visible at all rotational angles of the effecter. As disclosed in the '177 Patent, the bands may be formed by optical tape applied to the effecter. The two markers 44a, 44b permit tracking the movement of the effecter in five degrees of freedom-X, Y, Z, pitch (X rotation) and yaw (Y rotation). The markers 44a, 44b are provided at a predetermined distance from the working tip 43 so that the localizer software can use the detected location of the two markers to extrapolate the 5 DOF position of the working tip. As explained in the '177 Patent, the markers 44a, 44b are cylindrical and mounted on a cylindrical tool. The cylindrical nature of the markers means that they can be visualized by the optical tracking device at any roll orientation of the tool and at a full 360° viewing angle relative to the tool. The markers thus provide on-axis tracking of the instrument regardless of the orientation of the tool or instrument on which the markers are mounted and regardless of the position of the optical tracking device. The longitudinal offset of the markers relative to each other provide a direct indication of the axis of the tool, which can then be tracked in five degrees of freedom.

Figure 3:
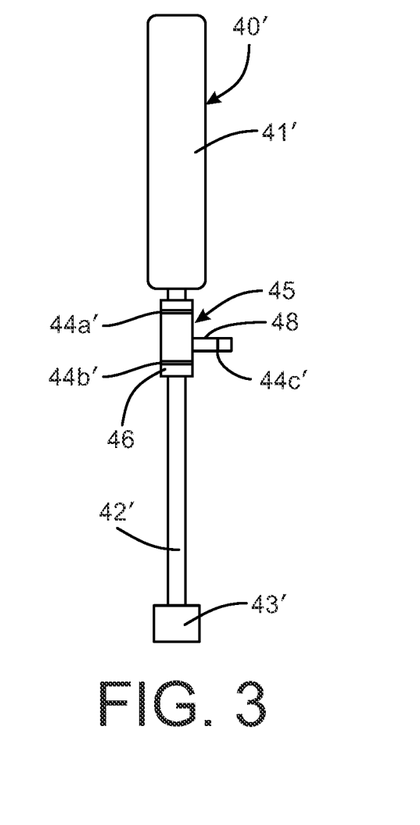
FIG. 3 is a side view of a generic effecter having a tracking element mounted on the effecter and providing marker bands for tracking the position of the effecter.

In another approach disclosed in the '177 Patent, the markers are incorporated into a tracking element 45 that can be mounted to the shaft 42' of a tool 40' that is otherwise similar to the tool 40, as shown in FIG. 3. The tacking element includes a cylindrical or partially cylindrical body 46 that can be mounted on the shaft 42' in a fixed position relative to the working tip 43'. The cylindrical body 46 includes the two markers 44a', 44b' in the form of bands that encircle the body. A third marker 44c' can be provided on an arm 48 that projects from the cylindrical body so that it is offset from the longitudinal axis of the shaft 42', with the third marker constituting an optically detectable band. The addition of the third marker 44c' adds a sixth degree of freedom to the position data detected by the localizer device, namely roll or rotation about the Z-axis or longitudinal axis of the shaft 42'. The bands 44a', 44b' can be spaced apart in the manner described above to denote a particular effecter.

Figure 5A:
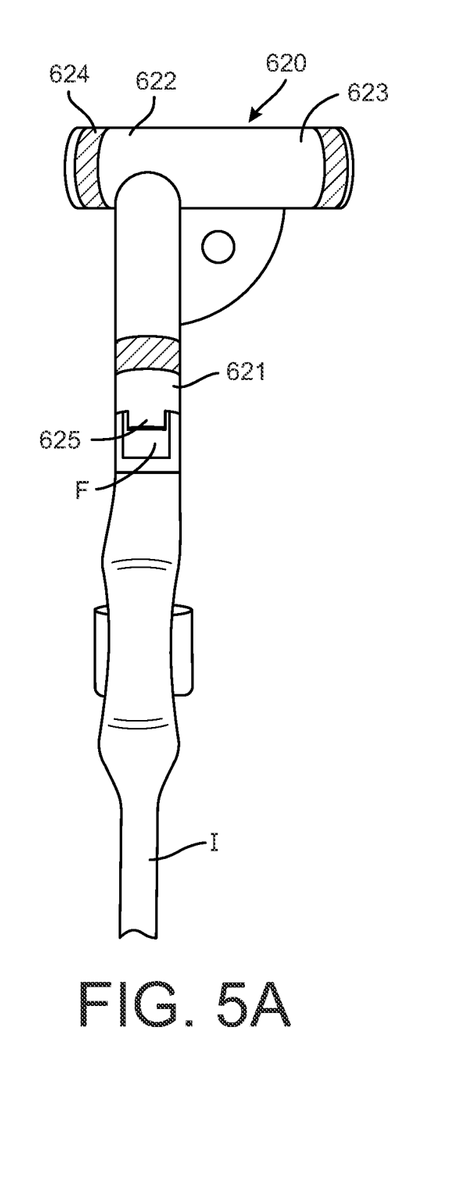
FIGS. 5A, 5B are side views of another tracking element in alternate positions on the end of an instrument.
Figure 5B:
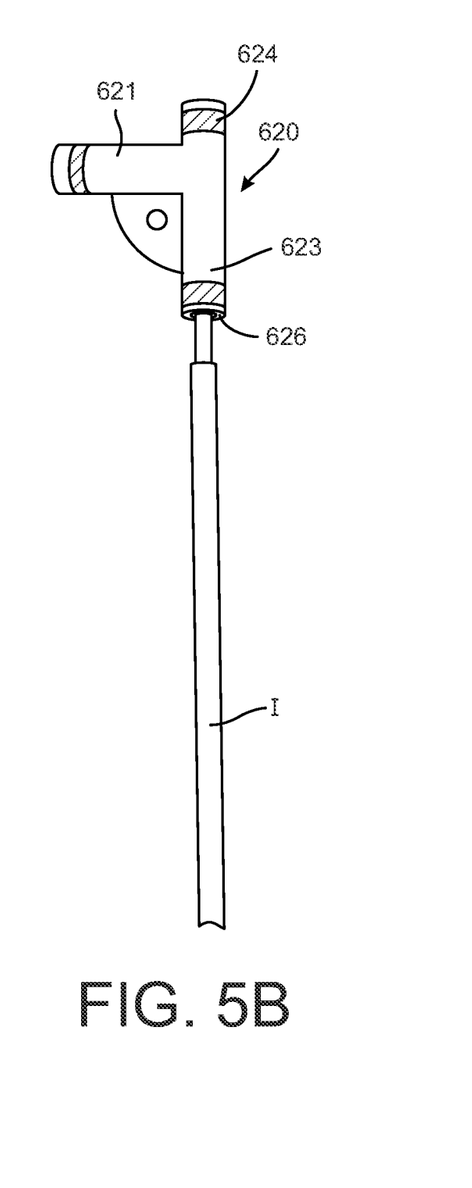

FIGS. 5A, 5B show another three-marker tracking element 620 that is configured to be mounted to the proximal end of an instrument I. The tracking element 620 includes three arms 621, 622 and 623 with detectable cylindrical markers 624 affixed to the arms. Arms 622 and 623 are aligned along a common axis and arm 621 is oriented perpendicular to that common axis. This configuration allows the same tracking element 620 to be used in a 6DOF mounting orientation, as shown in FIG. 5A, or in a 5 DOF orientation, as shown in FIG. 5B. In the 6 DOF orientation, the arm 621 includes a tang 625 that can engage a flat F at the end of the instrument I, as illustrated in FIG. 5A. This engagement allows the tracking element 620 to rotate with the instrument, thus providing the sixth (roll) degree of freedom. On the other hand, in the 5 DOF orientation, the arm 623 is provided with a cylindrical bore 626 that is seated on the end of the instrument I shown in FIG. 53B but without the tang. The tracking element 620 is thus free to rotate apart from the instrument. It can be appreciated that in either configuration there is at least one cylindrical tracking marker that is off-axis from the longitudinal axis of the tool/instrument on which the tracking element 620 is mounted.

Figure 4A:
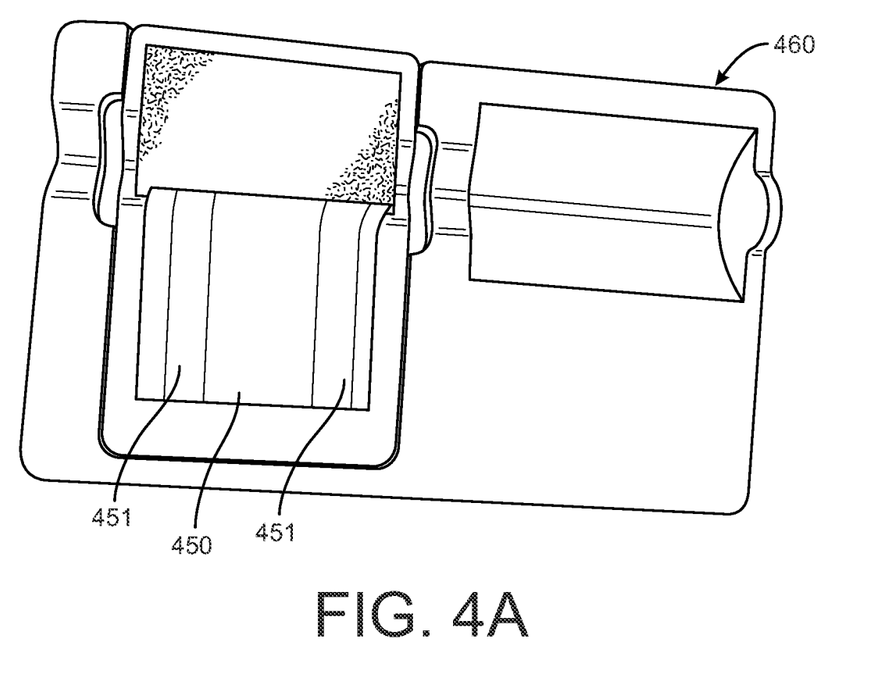
FIGS. 4A-4D are views of an applicator for applying a tracking sticker to an instrument according to another aspect of the present disclosure.
Figure 4B:
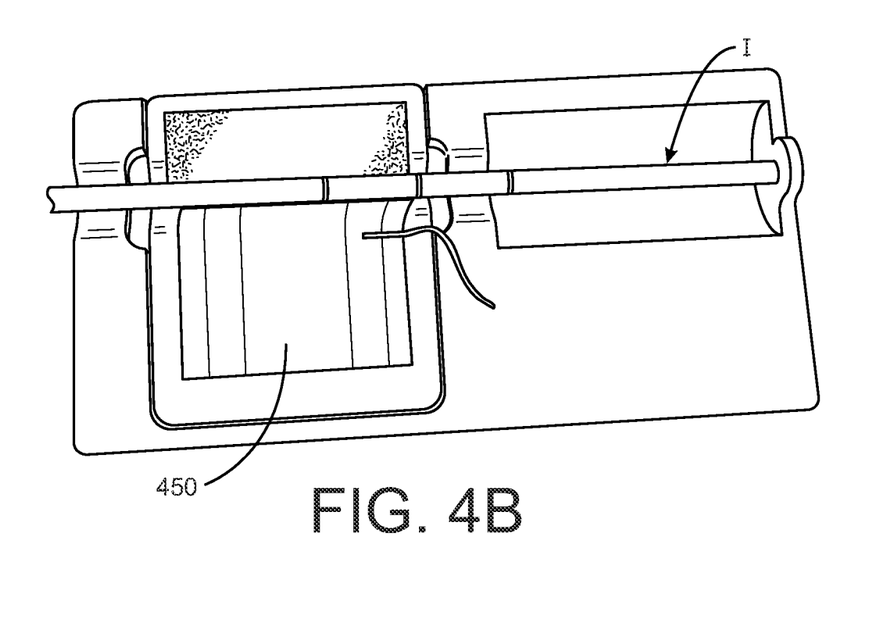
Figure 4C:
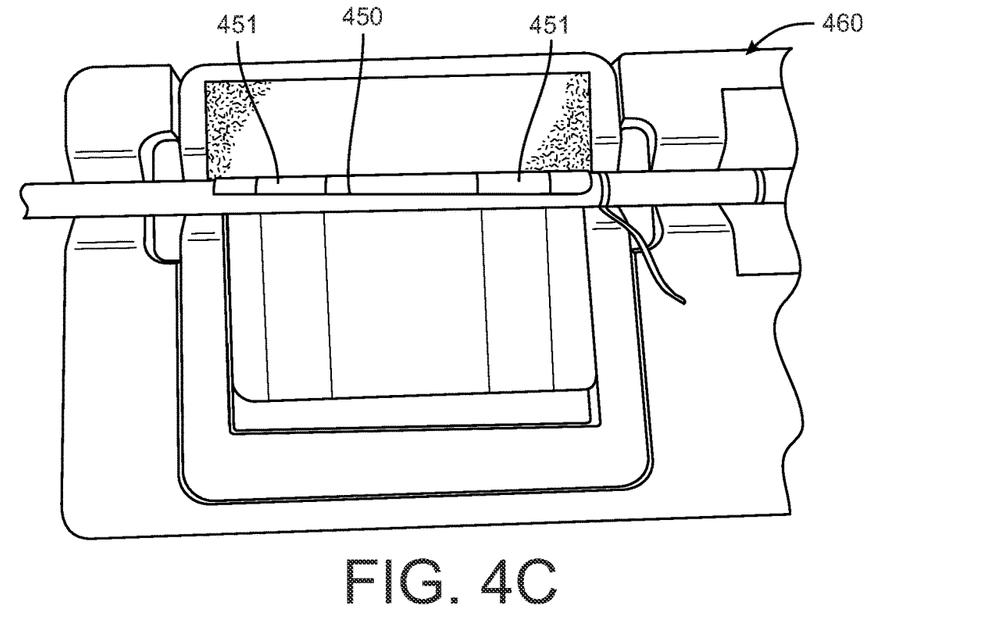
Figure 4D:
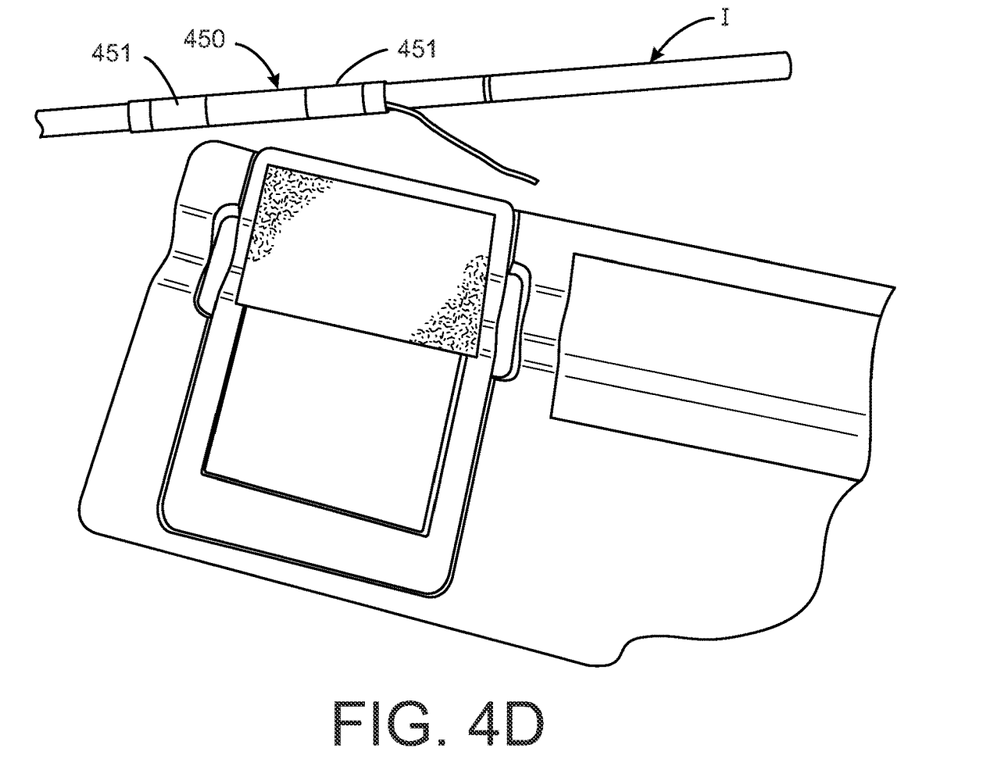

As disclosed in the '177 Patent, the tracking elements described above can be in the form of a sheet or a sticker 450 with detectable bands 451, as shown in FIG. 4A. The sticker is applied continuously around the circumference of the shaft of an instrument, such as the instrument I in FIGS. 4B-4D. It is understood that the sticker is formed of a material that is transparent to X-rays and to the optical detector 130, while the detectable bands 451 are transparent to X-rays but detectable by the optical detector (or similar detector that does not interfere with X-rays). The stickers and detectable bands 451 are configured so that the bands are orthogonal to the longitudinal axis of the instrument so that an accurate location of the working tip can be established. The bands also encircle the instrument, providing for full 360° detectability. An applicator assembly 460 as shown in FIGS. 4A-4D is provided to facilitate placement of the sticker 450 on the shaft of the instrument. Details of the applicator assembly are disclosed in the '177 Patent.

In another approach, the stickers, such as sticker 450, can be provided with a removable backing or removably mounted on a sheet. The sticker can thus be manually removed and wrapped around any cylindrical portion of an effecter or tracking element, such as elements 45 or 620.

Figure 8A:
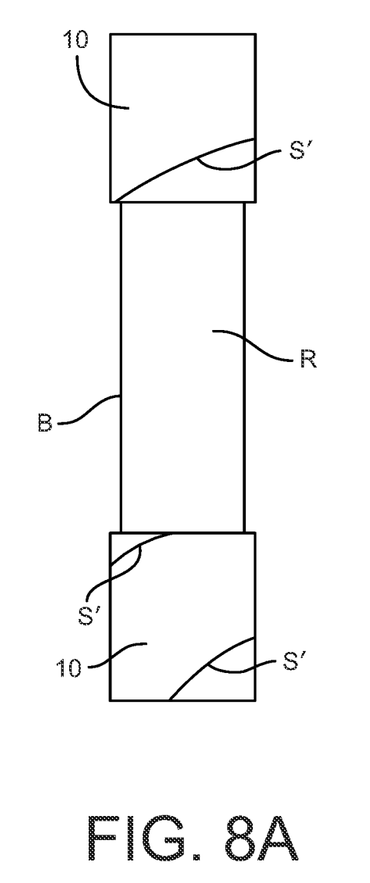
FIG. 8A is a top view of a tracking element with rhomboid markers according to the present disclosure mounted thereon, showing the helical seam formed by the marker.
Figure 8B:
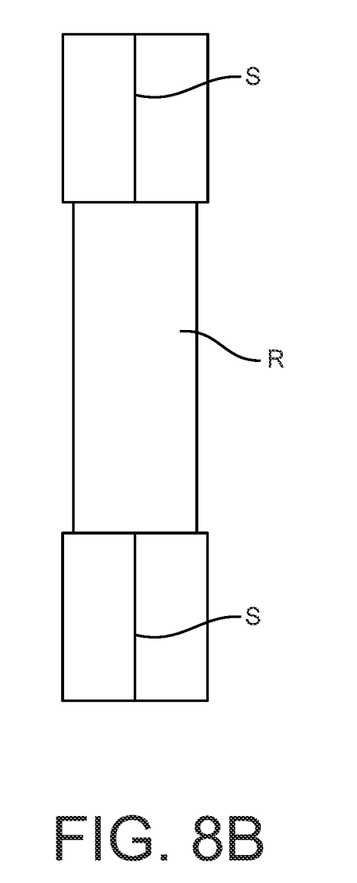
FIG. 8B is a top view of a prior marker mounted on a tracking element, showing the vertical seam formed by the marker.

In the embodiments disclosed in the '177 Patent, the trackable markers, such as markers 44a, 44b, and the bands, such as bands 451, 624, are rectangular sheets or stickers that are wrapped uniformly about the cylindrical portion of the effecter or tracking element. When the rectangular markers or stickers are wound around and affixed to the shaft of the instrument, a seam S inherently appears at the exposed end edges of the stickers, as shown in FIG. 8B. For the rectangular band, the seam S extends generally vertically along the length of the instrument shaft at one circumferential location. It has been found that this edge can present difficulties to the tracking software using the data received from the localizer 130 (FIG. 1). Current tracking software essentially seeks to locate the centroid of the marker and uses the coordinates of that centroid to determine the location and orientation of the instrument on which the markers are mounted. When all of the cameras of the localizer (usually two cameras) see only a smooth surface of the marker, the tracking software has no trouble properly locating the marker and instrument. However, when one camera sees the generally vertical seam, the software has difficulty determining the proper centroid of the marker/sticker, in part because the seam Sis only visible to one camera of the localizer. In practice it has been found that two cameras of a localizer visualizing the same sticker often identify centroids of the same sticker that are off by up to 1 cm. The software must resolve this discrepancy between measured centroids of the common marker, which will necessarily not be at the actual centroid of the marker. The problem becomes more pronounced when the instrument is tilted from one location to another, which can lead to a significant error in identifying the location of the marker, instrument and ultimately the working tip. An error of this nature can mean that the effecter or instrument is not being properly positioned for the surgical procedure.

Figure 6:
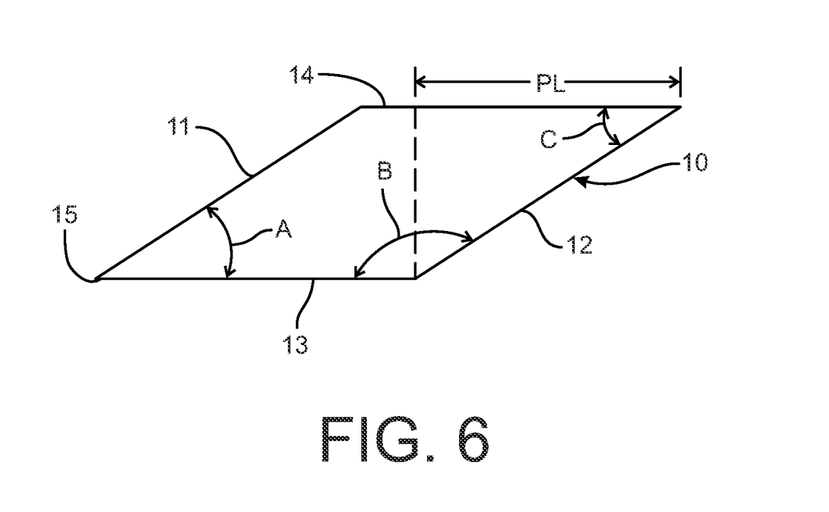
FIG. 6 is a plan view of a rhomboid marker according to the present disclosure for mounting on an effecter, such as the effecter of FIG. 2, or tracking element, such as the tracking element of FIG. 3.

In order to address this potential for error, the present disclosure provides a marker that presents an edge that does not extend generally vertically at one circumferential location. More particularly, the edge extends 360° around the cylindrical effecter or tracking body. Thus, as shown in FIG. 6, the present disclosure contemplates a marker 10 that is rhomboid in shape in one embodiment. As shown in FIG. 8A, when the marker is wrapped around the arm R of the tracking body B, a seam S' appears as a spiral, visible at all viewing angles. Although the seam S' is not at the same location around the circumference of the arm, the tracking software is still able to account for the presence of a seam detected by each of the localizer cameras and can accurately determine the centroid of the marker. The difference between the seam S of the rectangular marker and the seam S' generated by the marker 10 can be seen by comparing FIGS. 8A and 8B.

Figures 7A, 7B:
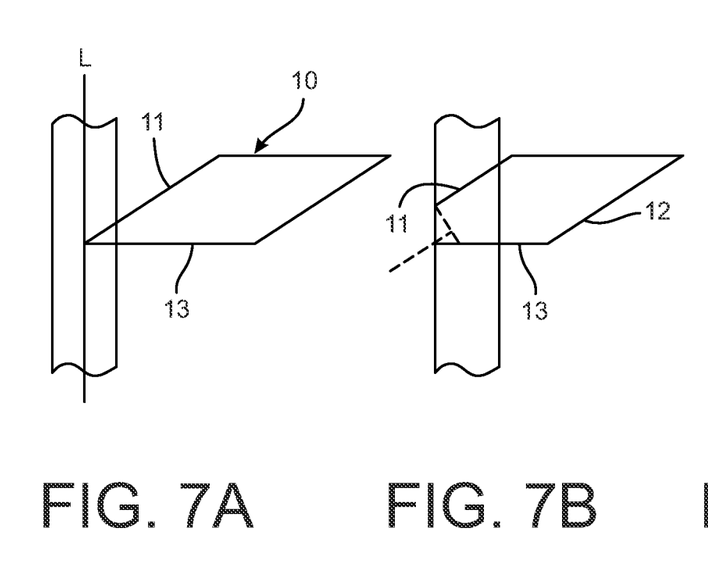
FIGS. 7A-7C show steps in affixing the rhomboid marker of FIG. 6 to the shaft of an effecter.
Figure 7C:
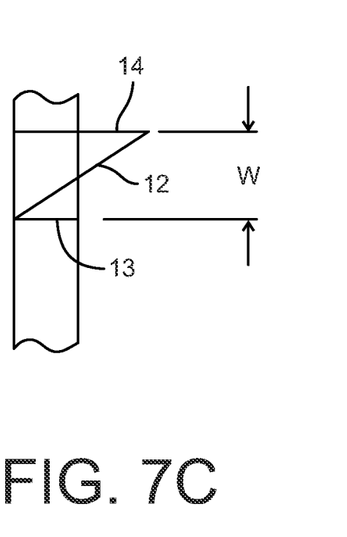

In one embodiment, the first edge 11 is parallel with the second edge 12, while a lower edge 13 and an upper edge 14 are parallel with each other. The edge 11 extends between the lower and upper edges 13, 14 and forms an angle A of about 30° relative to the lower edge 13. The edge 12 also extends between the lower and upper edges 13, 14 and forms an angle B of about 150° relative to the lower edge 13. The marker/sticker 10 is mounted on an elongated arm or shaft starting at the vertex 15 with the edge 13 arranged generally perpendicular to the longitudinal axis L of the arm, as shown in FIG. 7A. The marker 10 is wound around an elongated shaft or arm of the surgical effecter or a tracking element so that the lower and upper edges 13, 14 are substantially perpendicular to the longitudinal axis of the shaft. As the marker is wound around the shaft, the first edge 11 forms a spiral that is eventually overlapped by the body of the marker after the first 360° around the circumference (FIG. 7B). As the marker is wrapped further around the shaft, it overlaps the first edge 11 until ultimately only edges 12, 13 and 14 are visible (FIG. 7C). The edge 12 forms the spiral that is visible to the localizer, while the edges 13, 14, are parallel to each other and perpendicular to the longitudinal axis, providing a uniform width W around the circumference of the shaft (FIG. 8C). In an important feature of the marker 10, the visible edge 12 is oriented non-perpendicular and non-colinear to the longitudinal axis L of the shaft or arm.

It can be appreciated that the projected length PL of the edge 12 projected onto the edge 14 is at least equal to the circumference of the effecter or tracking body on which the marker 10 is applied—i.e., PL≥πD, where D is the diameter of the effecter or tracking body on which the marker is applied. It can also be appreciated that the marker can have an overall length that allows the marker to overlap itself. As seen in FIG. 6, the length of the edges 13, 14 is greater than the projected length PL (and thus greater than the circumference of the shaft), and it is this extra length that allows the marker to overlap itself. The length of the edges 13, 14 can be long enough so that the marker can overlap itself more than once when applied to an effecter. This aspect allows a longer marker to be used for a wide range of effecter instrument diameters without compromising the essential function of the marker. It can be noted that this overlap can lead to two spiral segments of the edge 13 being visible from certain aspects, but the tracking software is capable of compensating for the additional visible segment.

The rhomboid shape of the illustrated embodiment provides an advantage that the marker can be applied to a shaft with the edges 11, 12 reversed—i.e., with the edge 12 to the left and the edge 11 constituting the visible edge-provided that the lower and upper edges 13, 14 are maintains perpendicular to the longitudinal axis. In some embodiments, all four edges can have the same length so that the marker can be applied in any orientation, provided that two edges are perpendicular to the longitudinal axis.

However, it can be appreciated that the marker 10 does not need to be in an exact rhomboid shape in order to secure the advantages of the present invention. For instance, although the edges 11, 12 are shown as being linear in the illustrated embodiment, the edge 11 does not need to be linear or even oriented at the specific angle A. Instead, the edge 11 can be non-linear and oriented at essentially any angle, including perpendicular, relative to the bottom edge 13. As described above, the marker 10 is wound around the instrument shaft so that only edges 12, 13 and 14 are visible. Thus, the particular angular orientation or contour of the edge 11 is not limited to the purely rhomboid configuration of the disclosed embodiment. In the illustrated embodiment in which the marker 10 is a rhomboid, the angle C between the edge 12 and the upper edge 14 is equal to the angle A. More specifically, the angles A and C are each complementary to the angle B—i.e., they sum 180°. In embodiments in which the angle A is not complementary to the angle B, the angle C must remain generally complementary to the angle B.

As with edge 11, the exposed angled edge 12 need not be entirely linear, but can instead be non-linear, albeit at a non-perpendicular angle B. The important feature of the edge 12 is that it runs entirely around the circumference of the instrument shaft to form a spiral edge. So, the angle B can vary from the 150° angle of the described embodiment as long as the projected length PL is at least equal to the circumference of the instrument shaft. It is also important that the width W be sufficiently large to facilitate detection by the localizer cameras. For most tracking devices, a width W of 1-2 cm can be readily detected by the localizer cameras. Thus, the angle B or its complementary angle C of the edge 12 must be sufficient to accommodate the suitable projected length PL (i.e., at least equal to the shaft circumference) and the suitable width dimension W (1-2 cm). It can be appreciated that the angle C, width W and projected length PL are related by the equation: $\tan(C)=W/PL=W/\pi D$. For example, for an instrument with a shaft diameter D of 2 cm, the projected length PL is about 6.5 cm, so for an angle B of 150° the width W of the marker should be about 3.5 cm.

As noted above the angle C is generally complementary to the angle B. For a non-linear edge 12, the same complementary relationship between angles B and C is maintained, albeit based on a linear projection of the non-linear edge 12 between its intersection with the lower and upper edges 13, 14.

The marker 10 can be provided on a sheet or sticker, such as sheet 450 in FIG. 4A, for application by the applicator assembly 460. The sheet can ensure that the marker is oriented properly for attachment to the tool/instrument/tracking element, namely with the edge 13 arranged perpendicular to the longitudinal axis of the effecter. It is contemplated that a single marker 10 can be provided on a sheet 450. Alternatively, as shown in FIGS. 4A-4D, the sheet 450 can include two markers 451 at a predetermined distance apart indicative of the type of instrument or effecter on which the markers are affixed. In this embodiment, the entire sheet 450 can be considered to be the marker 10, with the entire sheet 450 configured to provide the spiral edge described above when the sheet is applied to the effector or instrument I. Although the portion of the sheet between the markers 451 are not detected, requiring the entire sheet 450 to generate the spiral edge ensures that the markers themselves exhibit the spiral edge for detection by the localizer system.

The present disclosure should be considered as illustrative and not restrictive in character. It is understood that only certain embodiments have been presented and that all changes, modifications and further applications that come within the spirit of the disclosure are desired to be protected. For instance, it is contemplated that the marker 10 can be affixed to a component, such as a tool, instrument, implant or tacking element, that does not have a circular cross-section. However, the component has an effective circumference, in the form of the perimeter length of the component, that can be measured and used to ensure that the projected length PL of the marker is sufficient for the marker to overlap itself on the component. Thus, for a non-circular cross-section, the projected length PL≥perimeter length.

What is claimed is:

1. A surgical effecter, comprising:
   an elongated shaft having a circumference and defining a longitudinal axis; and
   a marker including a sheet wrapped around the circumference of the shaft, the sheet including;
   a perimeter;
   a lower edge and an opposite upper edge at the perimeter that are parallel to each other and that are arranged perpendicular to the longitudinal axis of the shaft; and
   a visible edge at the perimeter extending between the lower and upper edges at a non-perpendicular and non-colinear angle relative to the longitudinal axis of the shaft, wherein said sheet is formed of a material that is detectable by cameras or detectors of a localizer or tracking system configured to track the position and orientation of the effecter during a surgical procedure.

2. The surgical effecter of claim 1, wherein said visible edge defines a non-perpendicular angle relative to said lower edge and a complementary angle relative to said upper edge.

3. The surgical effecter of claim 2, wherein said non-perpendicular angle is 150° and the complementary angle is 30°.

4. The surgical effecter of claim 1, wherein said sheet is configured as a rhomboid.

5. The surgical effecter of claim 1, wherein said lower edge and upper edge have a length that is greater than the circumference of the elongated shaft.

6. The surgical effecter of claim 1, wherein said marker overlaps itself on the circumference of the elongated shaft.

7. The surgical effecter of claim 1, wherein said lower edge and said upper edge are linear.

8. The surgical effecter of claim 1, wherein said visible edge is linear.

9. The surgical effecter of claim 1, wherein said visible edge is non-linear.

10. The surgical effecter of claim 1, wherein said sheet is a sticker configured to be applied to said elongated shaft.

* * * * *